United States Patent
Chen (10) Patent No.: US 10,624,391 B2
(45) Date of Patent: Apr. 21, 2020

(54) INHALER, ATOMIZING ASSEMBLY AND ATOMIZING CORE

(71) Applicant: SHENZHEN SMOORE TECHNOLOGY LIMITED, Shenzhen (CN)

(72) Inventor: Zhiping Chen, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 576 days.

(21) Appl. No.: 15/323,693

(22) PCT Filed: Sep. 26, 2014

(86) PCT No.: PCT/CN2014/087499
§ 371 (c)(1),
(2) Date: Jan. 3, 2017

(87) PCT Pub. No.: WO2016/045076
PCT Pub. Date: Mar. 31, 2016

(65) Prior Publication Data
US 2017/0196266 A1    Jul. 13, 2017

(51) Int. Cl.
*A61M 15/00* (2006.01)
*A61M 11/00* (2006.01)
(Continued)

(52) U.S. Cl.
CPC ............ *A24F 47/008* (2013.01); *A24F 47/00* (2013.01); *A61M 11/041* (2013.01);
(Continued)

(58) Field of Classification Search
CPC .............. A61M 15/00; A61M 15/0001; A61M 15/0003; A61M 15/0011; A61M 15/0021; A61M 16/201; A61M 15/0065; A61M 15/0068; A61M 15/0071; A61M 15/009; A61M 15/0091; A61M 15/06;
(Continued)

(56) References Cited

U.S. PATENT DOCUMENTS

| 2012/0318283 A1* | 12/2012 | Watanabe | A24F 47/002 131/191 |
| 2013/0192615 A1* | 8/2013 | Tucker | H05B 3/42 131/328 |
| 2014/0060524 A1* | 3/2014 | Liu | A24F 47/008 128/200.14 |
| 2014/0109898 A1* | 4/2014 | Li | A24F 47/008 128/200.14 |

(Continued)

*Primary Examiner* — Tu A Vo
(74) *Attorney, Agent, or Firm* — Weiss & Moy, P.C.; Jeffrey D. Moy (57) ABSTRACT

An atomizing assembly has an inhaler, an atomizing assembly and an atomizing core. The atomizing assembly has a shell. The atomizing core joins with the shell. The shell has a gas flow passage and a liquid storage cavity which encircles the gas flow passage and serves for liquid storage. The atomizing core has a core body, an exhaust tube and an atomizing element. The core body is provided with an atomizing cavity, and the exhaust tube is disposed at a gas outlet. The atomizing element is disposed within the atomizing cavity and is used for liquid atomization; at least a part of the exhaust tube extends into the gas flow passage, and a through hole or a gap communicates with the interior of the exhaust tube. The gas flow passage is disposed on the sidewall of the exhaust tube.

13 Claims, 12 Drawing Sheets

(51) Int. Cl.
*A24F 47/00* (2020.01)
*A61M 11/04* (2006.01)
*A61M 15/06* (2006.01)

(52) U.S. Cl.
CPC ........ *A61M 15/0021* (2014.02); *A61M 15/06* (2013.01); *A61M 2205/3653* (2013.01); *A61M 2205/8206* (2013.01)

(58) Field of Classification Search
CPC ...... A61M 15/08; A61M 11/00; A61M 11/02; A61M 11/04; A61M 11/06; A61M 11/08; A61M 2205/502; A61M 2202/04; A61M 2205/3334; A61M 2202/0484; A61M 2205/505; A61M 2205/581; A61M 2202/0266; A61M 2205/583; A61M 2202/025; A61M 2202/0208; A61M 15/0066; A61M 15/0083; A61M 15/008; A61M 11/042; A61M 2205/8206; A24F 47/008; A24F 1/32; A24F 7/02; A24D 1/14; B01B 1/005
See application file for complete search history.

(56) References Cited

U.S. PATENT DOCUMENTS

| | | | | |
|---|---|---|---|---|
| 2014/0123989 A1* | 5/2014 | LaMothe | ............... | A24F 47/008 131/328 |
| 2014/0261495 A1* | 9/2014 | Novak, III | ............ | A24F 47/008 131/329 |
| 2014/0290677 A1* | 10/2014 | Liu | ........................ | A24F 47/008 131/329 |
| 2014/0311503 A1* | 10/2014 | Liu | ........................ | A24F 47/008 131/329 |
| 2014/0332018 A1* | 11/2014 | Liu | ........................ | A24F 47/008 131/329 |
| 2014/0360516 A1* | 12/2014 | Liu | ........................ | A61M 15/06 131/329 |
| 2015/0128971 A1* | 5/2015 | Verleur | ................ | A24F 47/008 131/329 |
| 2015/0184846 A1* | 7/2015 | Liu | ......................... | F22B 1/284 131/329 |
| 2015/0351454 A1* | 12/2015 | Huang | ................... | F22B 1/284 392/394 |
| 2016/0143357 A1* | 5/2016 | Liu | ........................ | H02J 7/0045 206/223 |

* cited by examiner

INHALER, ATOMIZING ASSEMBLY AND ATOMIZING CORE

FIELD OF THE INVENTION

The present disclosure relates to a field of devices for delivering atomized medium into a human body, and more particularly relates to an inhaler, an atomizing assembly, and an atomizing core.

BACKGROUND OF THE INVENTION

An inhaler is a device used for delivering atomized liquid into a human body, which mainly includes an electronic cigarette for substituting tobacco cigarette and a medical nebulizer for treating upper respiratory diseases.

When using the conventional electronic cigarettes or nebulizers having a similar structure, the inhaler may make some noise like bubbling, even worse, the user may frequently draws fluid into the mouth.

SUMMARY OF THE INVENTION

Accordingly, it is necessary to provide an inhaler, an atomizing assembly, and an atomizing core to address the aforementioned deficiency of making noise and easily drawing fluid into the mouth.

An atomizing assembly for an inhaler includes:

a housing defining an airflow channel therein and comprising a reservoir surrounding the airflow channel for storing liquid; and an atomizing core coupled to the housing and comprising a core body, an exhaust pipe, and an atomizing element, the core body defining an atomizing chamber therein, the core body further defining an inlet and an outlet thereon in fluid communication with the atomizing chamber, the exhaust pipe being located at the outlet, the atomizing element being received in the atomizing chamber and being configured to atomize the liquid;

wherein the core body further defines a liquid absorbing hole in fluid communication with the atomizing chamber and the reservoir, the atomizing element is in contact with the liquid in the reservoir via the liquid absorbing hole, the exhaust pipe extends at least partially into the airflow channel, the exhaust pipe defines a through hole or notch on a sidewall thereof which is in fluid communication with an interior of the exhaust pipe and the airflow channel.

An inhaler includes a power source assembly and the atomizing assembly for an inhaler; wherein the power source assembly is fixed to the atomizing assembly, and the power source assembly is electrically coupled to the atomizing element.

An atomizing core of an atomizing assembly for an inhaler includes a core body, an exhaust pipe, and an atomizing element;

wherein the core body defines an atomizing chamber therein, the core body further has an inlet and an outlet thereon in fluid communication with the atomizing chamber, the core body further defines a liquid absorbing hole in fluid communication with the atomizing chamber and an external;

wherein the exhaust pipe is located at the outlet, the exhaust pipe defines a through hole or notch on a sidewall thereof which is in fluid communication with an interior and an external of the exhaust pipe;

wherein the atomizing element is received in the atomizing chamber, and the atomizing element is in contact with external liquid via the liquid absorbing hole.

According to the foregoing inhaler, atomizing assembly, and atomizing core, the exhaust pipe defines the through hole or notch on the sidewall thereof which is in fluid communication with the interior of the exhaust pipe and the airflow channel, such that the condensed liquid in the airflow channel can return to the atomizing chamber, thus preventing the liquid from forming a film at the end of the exhaust pipe due to the large viscosity and surface tension, the film can block the liquid from flowing back from the end of the exhaust pipe to the atomizing chamber. In addition, the liquid will not accumulate in the airflow channel, such that the deficiency of making noise and easily drawing fluid into the mouth by the user during use can be solved.

DETAILED DESCRIPTION OF THE EMBODIMENTS

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As a component of an inhaler, an atomizing assembly according to an embodiment is used to atomize liquid and to deliver the atomized liquid into the human body. The inhaler may be in the form of an electronic cigarette, a medical nebulizer, or the like.

Figure 1:
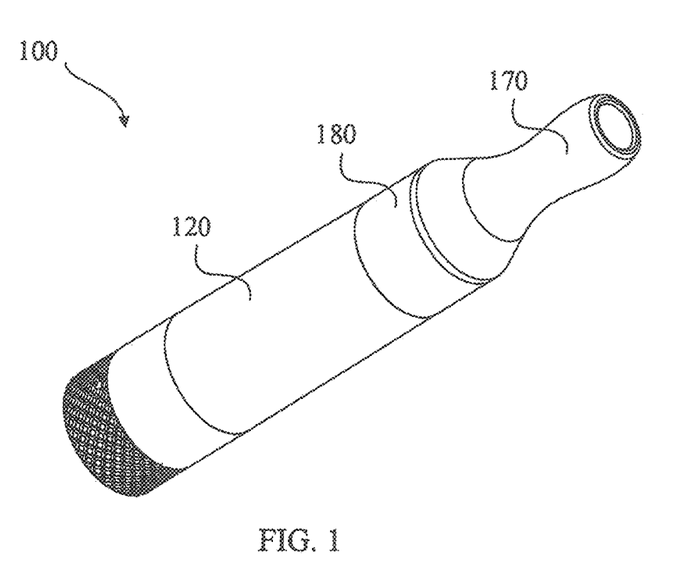
FIG. 1 is a perspective view of an atomizing assembly of an inhaler according to an embodiment.
Figure 2:
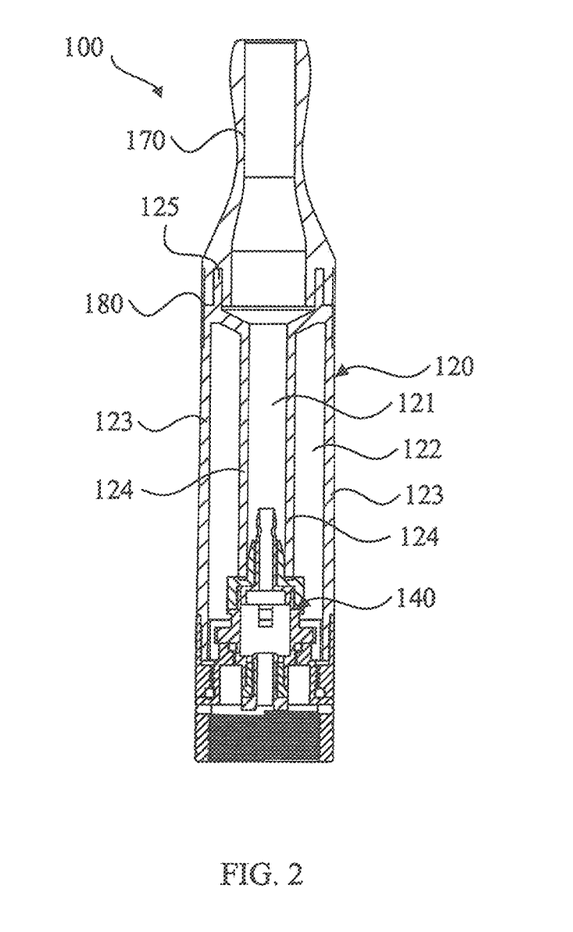
FIG. 2 is a cross-sectional view of the atomizing assembly of the inhaler of FIG. 1.
Figure 3:
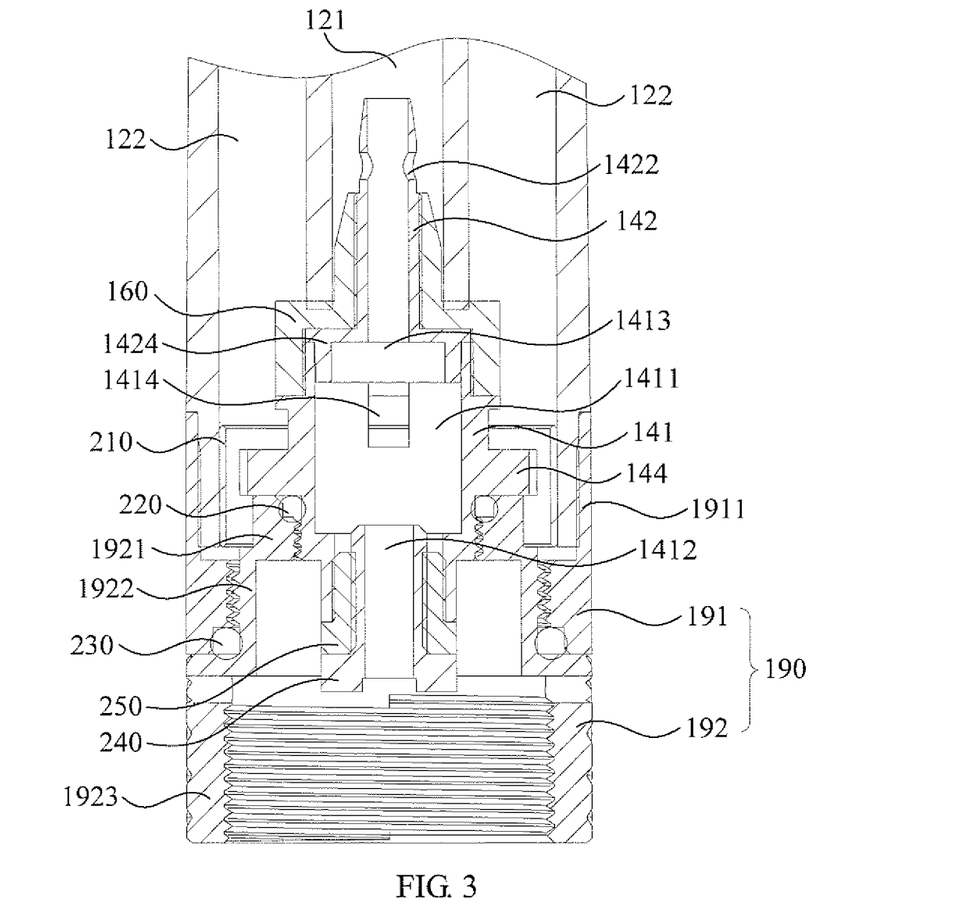
FIG. 3 is a partial enlarged view of the atomizing assembly of the inhaler of FIG. 2.

Referring to FIG. 1 to FIG. 3, an atomizing assembly 100 according to one embodiment includes a housing 120 and an atomizing core 140 coupled to the housing 120. The housing 120 defines an airflow channel 121 therein and has a reservoir 122 surrounding the airflow channel 121 for storing liquid. If the inhaler is an electronic cigarette, then the liquid stored in the reservoir 122 can be the tobacco liquid; if the inhaler is a medical nebulizer, then the liquid stored in the reservoir 122 can be the liquid medicine.

Figure 4:
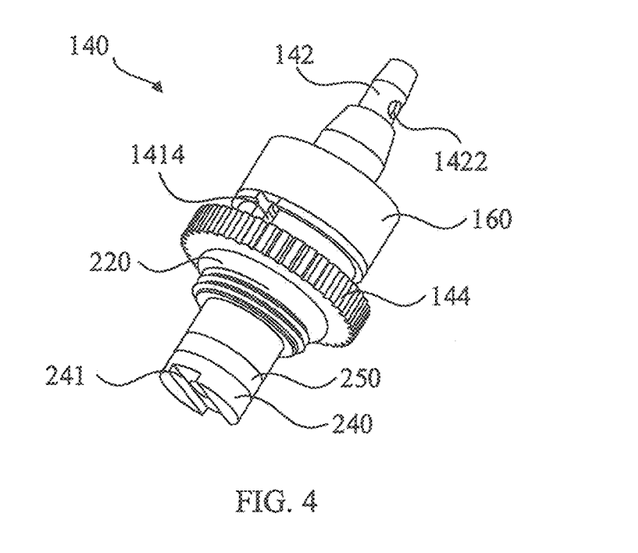
FIG. 4 is a perspective view of an atomizing core of the atomizing assembly of the inhaler of FIG. 1.
Figure 5:
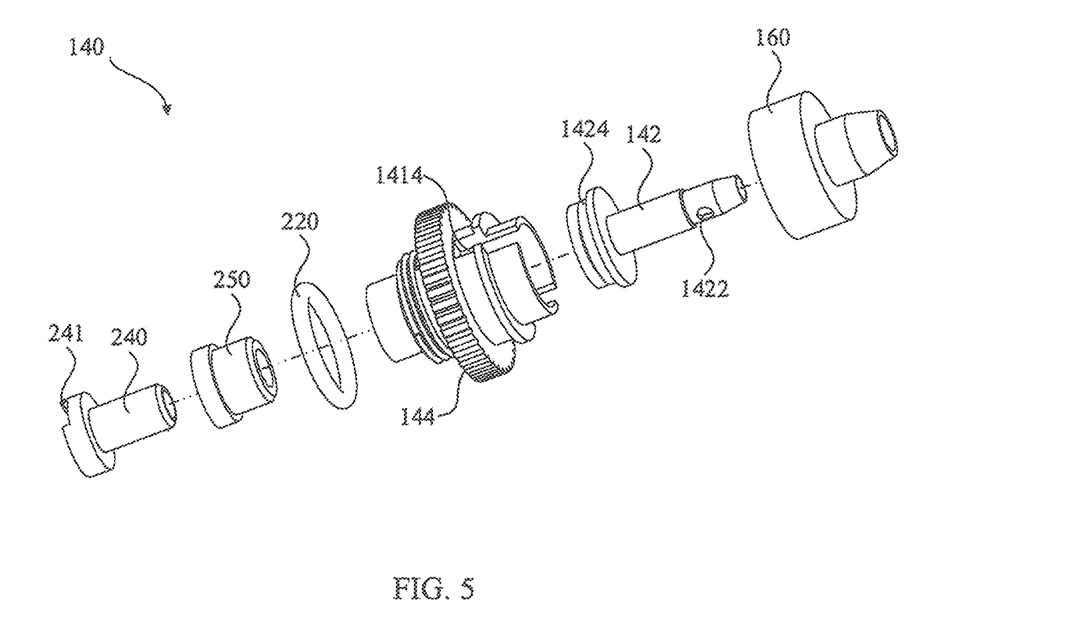
FIG. 5 is an exploded view of the atomizing core of the atomizing assembly of the inhaler of FIG. 4.
Figure 6:
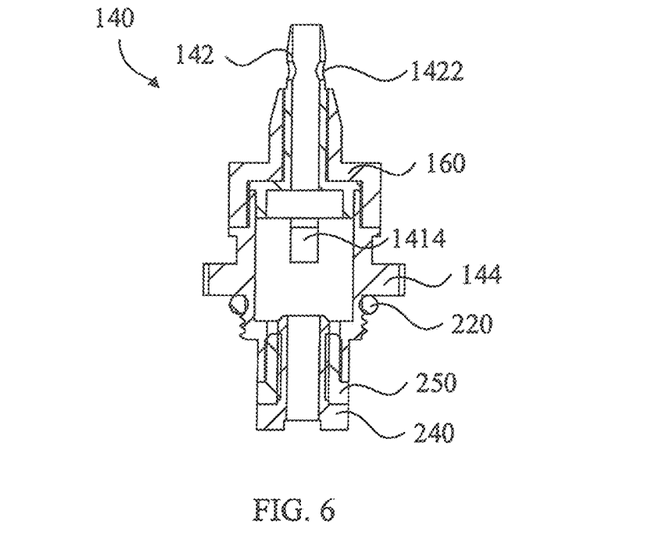
FIG. 6 is a cross-sectional view of the atomizing core of the atomizing assembly of the inhaler of FIG. 4

Referring also to FIG. 4 to FIG. 6, the atomizing core 140 includes a core body 141, an exhaust pipe 142, and an atomizing element (not shown in FIG. 4 to FIG. 6). The core body 141 defines an atomizing chamber 1411 therein. The core body 141 further defines an inlet 1412 and an outlet 1413 thereon in fluid communication with the atomizing chamber 1411. The exhaust pipe 142 is located at the outlet 1413. The atomizing element is received in the atomizing chamber 1411 and is configured to atomize the liquid. The core body 141 is partially received in the housing 120. The core body 141 further defines a liquid absorbing hole 1414 in fluid communication with the atomizing chamber 1411 and the reservoir 122. The atomizing element is in contact with the liquid in the reservoir 122 via the liquid absorbing hole 1414. The exhaust pipe 142 extends at least partially into the airflow channel 121. The exhaust pipe 142 defines a through hole 1422 on a sidewall thereof, which is in fluid communication with an interior of the exhaust pipe 142 and the airflow channel 121.

The through hole 1422 defined on the sidewall of the exhaust pipe 142 can enable the condensed liquid in the airflow channel 121 to return to the atomizing chamber 1411, thus preventing the liquid from forming a film at an end opening of the exhaust pipe 142 due to the large viscosity and surface tension of the liquid, and the film can block the liquid from flowing back from the end opening of the exhaust pipe 142 to the atomizing chamber 1411. The liquid will not accumulate in the airflow channel 121, such that the problem of making noise and easily drawing fluid into the mouth by the user during use can be solved.

Referring to FIG. 2, in one embodiment, the housing 120 can include a first tubular structure 123 and a second tubular structure 124. The first tubular structure 123 has a diameter greater than that of the second tubular structure 124, thus the second tubular structure 124 can be located inside the first tubular structure 123. The first tubular structure 123 and the second tubular structure 124 can be coaxially arranged. The airflow channel 121 is formed by an interior of the second tubular structure 124, and the reservoir 122 surrounding the airflow channel 121 for storing liquid is formed between the second tubular structure 124 and the first tubular structure 123. An end of the reservoir 122 away from the core body 141 is sealed. The housing 120 can be made of transparent plastic, such that on the one hand it is easy to process, on the other hand, the user can observe the amount of the remaining liquid in the reservoir 122, thus facilitating replacing the atomizing assembly 100 or refilling the reservoir 122 with liquid.

Referring to FIG. 3 to FIG. 6, the atomizing core 140 can include a sealing member 160, which is sleeved on the exhaust pipe 142. Partial exhaust pipe 142 extends out of the sealing member 160. The sealing member 160 is located between the exhaust pipe 142 and the second tubular structure 124, and the sealing member 160 abuts an inner sidewall of the second tubular structure 124. By the configuration of the sealing member 160, the liquid in the reservoir 122 is prevented from entering the airflow channel 121. The through hole 1422 can be located at a portion of the exhaust pipe 142 extending out of the sealing member 160 and the through hole 1422 is adjacent to the sealing member 160. The liquid in the airflow channel 121 generally accumulates near the sealing member 160, the configuration of through hole 1422 can enable the accumulated liquid to easily flow back to the atomizing chamber 1411, thus the amount of the accumulated liquid can be reduced.

The core body 141 and the exhaust pipe 142 can be made of plastic. In order to facilitate mold stripping during the processing, the core body 141 and the exhaust pipe 142 can be of split type. A latching boss 1424 is provided at an end of the exhaust pipe 142, and the latching boss 1424 can be latched in the outlet 1413. The sealing member 160 can extend to a junction of the core body 141 and the exhaust pipe 142, thus preventing the liquid in the reservoir 122 from entering the atomizing chamber 1411 via a gap at the junction.

Figure 7:
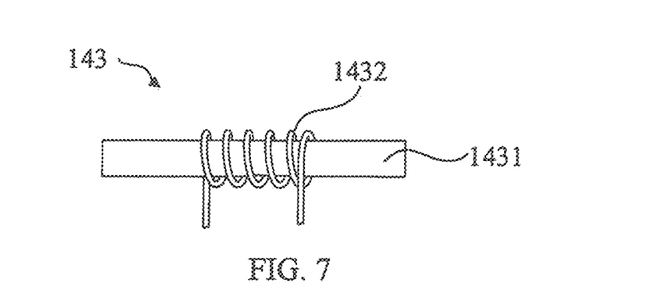
FIG. 7 is a front view of an atomizing element.

In one embodiment, there are two opposing liquid absorbing holes 1414 defined on the core body 141. Referring also to FIG. 7, the atomizing element 143 generally includes a column-like liquid-absorbing cotton 1431 and a heating wire 1432 wound on the liquid-absorbing cotton 1431. Two liquid absorbing holes 1414 are oppositely arranged, two ends of the liquid-absorbing cotton 1431 extend through the two liquid absorbing holes 1414, respectively to be in contact with the liquid in the reservoir 122, thus increasing the atomizing efficiency. And the two liquid absorbing holes 1414 also can serve to fix the liquid-absorbent cotton 1431, such that it is not necessary to introduce an additional structure for fixing the atomizing element 143, thus the core body 141 is simple in construction and easy to process.

Figure 8:
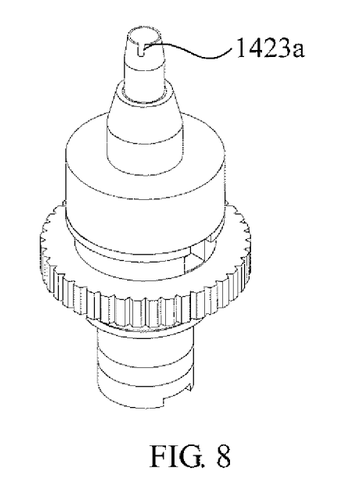
FIG. 8 is a perspective view of an atomizing core of the atomizing assembly of the inhaler according to another embodiment.
Figure 9:
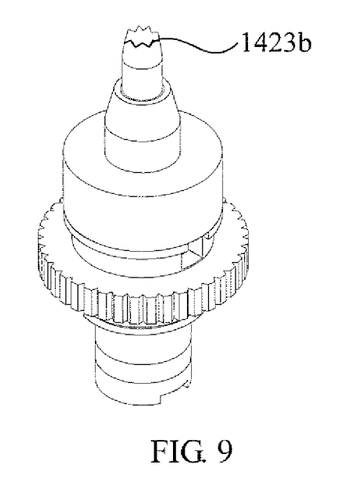
FIG. 9 is a perspective view of an atomizing core of the atomizing assembly of the inhaler according to another embodiment.
Figure 10:
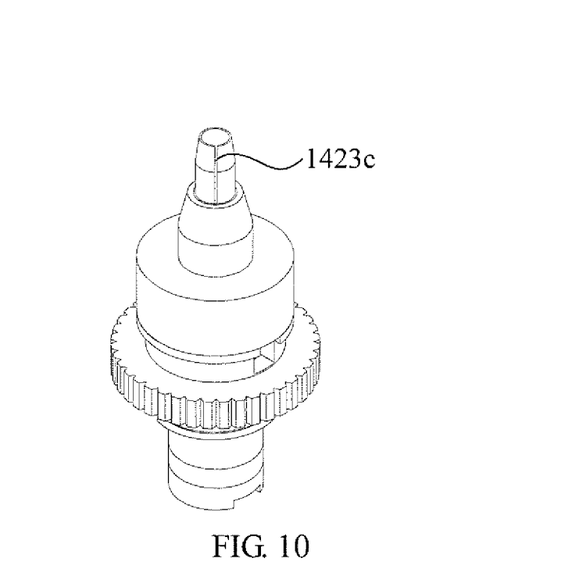
FIG. 10 is a perspective view of an atomizing core of the atomizing assembly of the inhaler according to another embodiment.
Figure 11:
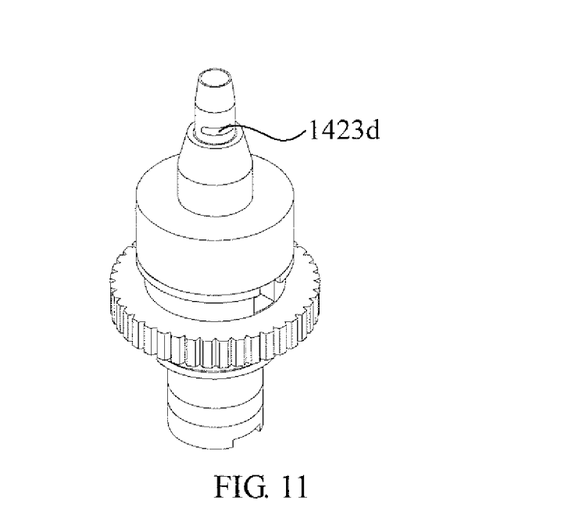
FIG. 11 is a perspective view of an atomizing core of the atomizing assembly of the inhaler according to another embodiment.

In one embodiment, the through hole 1422 can be replaced by a notch. Referring also to FIG. 8, a notch 1423a is located at an edge of the exhaust pipe 142. The number of the notch can be single, or plural. Referring also to FIG. 9, in one embodiment, the plurality of notches 1423b are serratedly arranged on the edge of the exhaust pipe 142. Referring also to FIG. 10, in one embodiment, the notch 1423c may have an elongated shape and extend along an axial direction of the exhaust pipe 142. The notch can enable the end opening of the exhaust pipe 142 not be located on a plane, such that a film is difficult to be formed which can block the return of the liquid flowing from the end opening of the exhaust pipe 142 into the atomizing chamber 1411. In one embodiment, the notch can be positioned at other locations on the exhaust pipe 142, as long as the notch is in fluid communication with the interior of the exhaust pipe 142 and the airflow channel 121. Referring also to FIG. 11, the exhaust pipe 142 has a cylindrical shape, and the notch 1423d may be an elongated strip extending along the circumference of the exhaust pipe.

Figure 12:
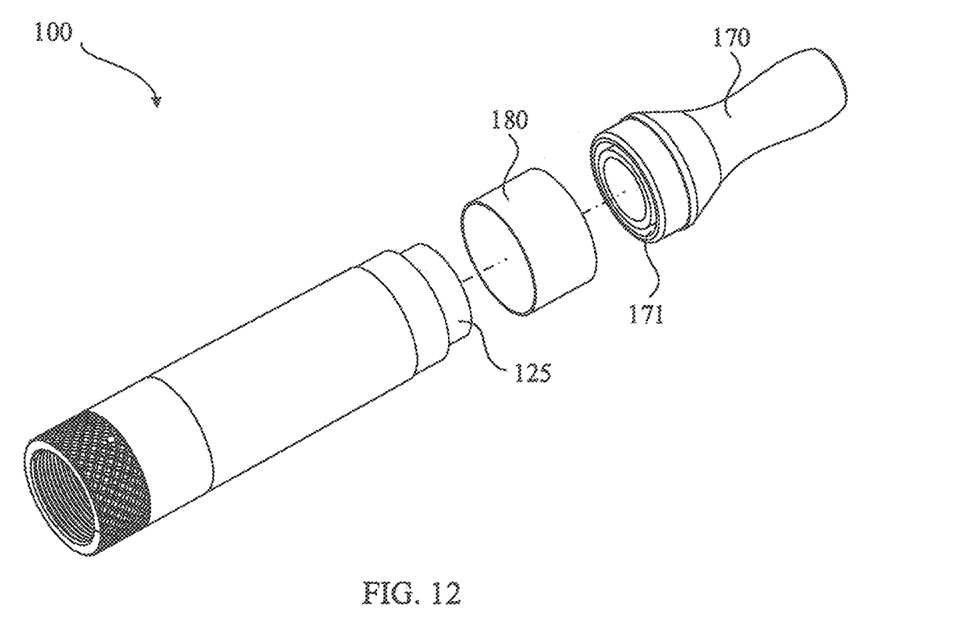
FIG. 12 is an exploded view of the atomizing assembly of the inhaler of FIG. 1.

For convenience of use, in one embodiment, the atomizing assembly 100 further includes a mouthpiece 170 located at an end of the housing 120 away from the atomizing core 140. Referring to FIG. 1, FIG. 2, and FIG. 12, in order to secure a connection between the mouthpiece 170 and the housing 120, the atomizing assembly 100 further includes a clamping member 180. The mouthpiece 170 defines an annular depressed latching groove 171 at an end thereof. The housing 120 is provided with an annular protruded latching portion 125 at an end thereof away from the core body 141. The latching portion 125 matches the latching groove 171 and is engaged in the latching groove 171, thereby connecting the mouthpiece 170 to the housing 120. The clamping member 180 has an annular shape. The clamping member 180 is located at a junction between the mouthpiece 170 and the housing 120, and the clamping member 180 is sleeved on an outside of the mouthpiece 170 and the housing 120.

The latching portion 125 is engaged in the latching groove 171, thereby connecting the mouthpiece 170 to the housing 120. The clamping member 180 is sleeved on the outside of the mouthpiece 170 and the housing 120, thus strengthening the connection between them. There are frictions between the clamping member 180 and the mouthpiece 170, and between the clamping member 180 and the housing 120, such that the resistance of reverse movement between the mouthpiece 170 and the housing 120 can be increased, thus preventing them from disengaging. In addition, once the latching portion 125 is engaged in the latching groove 171, if the atomization assembly 100 is shaken violently and an axial force is applied, the housing 120 and the mouthpiece 170 are easily disengaged from each other. However, after the configuration of the clamping member 180, the clamping member 180 can be tightly fitted to the housing 120, such that the housing 120 and the mouthpiece 170 are prevented from being displaced in the radial direction, thus ensuring a secured connection. Meanwhile, since the clamping member 180 can exert force on the outside of the mouthpiece 170 and the housing 120, the engagement between the latching portion 125 and the latching groove 171 will become more tight, the friction between the latching portion 125 and an inner sidewall of the latching groove 171 can be increased, thus further increasing the resistance of reverse movement between the mouthpiece 170 and the housing 120 and securing the connection between the mouthpiece 170 and the housing 120.

In one embodiment, the mouthpiece 170 and the housing 120 may further define a groove on a portion thereof in contact with the clamping member 180 to accommodate the clamping member 180. The clamping member 180 can be received in the groove, thus enhancing the rigidity of the clamping member 180.

In one embodiment, the number of the clamping member 180 can be plural. The plurality of the clamping members 180 have an annular shape and are coaxially arranged. In one embodiment, both of the latching portion 125 and the latching groove 171 have an annular shape. In alternative embodiments, the latching portion 125 and the latching groove 171 may have a columnar or rectangular shape. Of course, the annular latching portion 125 and the latching groove 171 can ensure a more firmly connection between the mouthpiece 170 and the housing 120. The latching portion 125 and the latching groove 171 have annular or other shapes, and the number of the latching portion 125 and the latching groove 171 can be plural. The plurality of the latching portions 125 and the plurality of latching grooves 171 correspond to each other. The plurality of the latching portions 125 and the plurality of latching grooves 171 can further enhance the rigidity of the connection.

Figure 13:
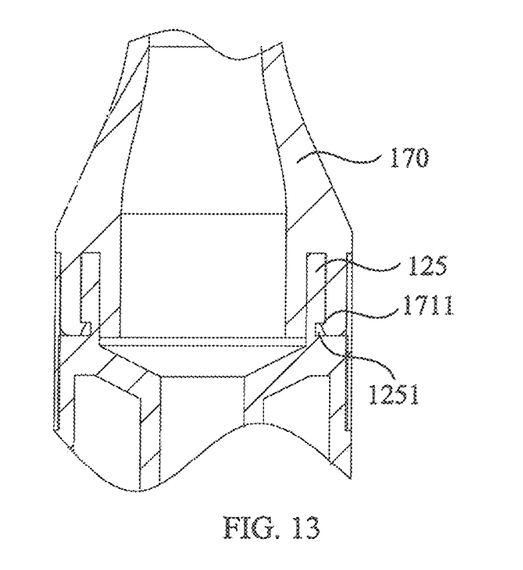
FIG. 13 is a partial enlarged view of the atomizing assembly of the inhaler of FIG. 1.

Referring to FIG. 13, in one embodiment, an inner sidewall of the latching groove 171 is provided with a protruding hook 1711, and the latching portion 125 defines a groove 1251 corresponding to the hook 1711. The mouthpiece 170 is made of plastic, which has certain elasticity. During the engagement between the latching portion 125 and the latching groove 171, a portion of the mouthpiece 170 provided with the hook 1711 can be deformed within a certain range, and the portion may be restored after the hook 1711 is latched in the groove 1251. Since the clamping member 180 is sleeved on the outside of the mouthpiece 170, the hook 1711 will not be disengaged from the groove 1251, thus further enhancing the rigidity of the connection. Preferably, the hook 1711 is adjacent to an end of the mouthpiece 170, which has a larger deformation range. In an alternative embodiment, the latching portion 125 and the latching groove 171 can be in an interference fit, therefore the pressure between the latching portion 125 and the inner sidewall of the latching groove 171 is increased, and the friction is increased. In addition, by the configuration of the clamping member 180, the pressure between the latching portion 125 and the inner sidewall of the latching groove 171 is further increased, and the friction is further increased, thus the connection between the mouthpiece 170 and the housing 120 becomes secured.

In alternative embodiments, the positions of the latching portion 125 and the latching groove 171 can be interchanged, i.e., the latching portion 125 can be located at the end of the mouthpiece 170, while the latching groove 171 is defined at the end of the housing 120, the connection effect of them are the same. In this embodiment, the mouthpiece 170 is located at the end of the housing 120 away from the atomizing core 140, and the protruded latching portion 125 is located at the end of the mouthpiece, the depressed latching groove 171 is defined at the end of the housing 120 away from the core body 141. The latching portion 125 matches the latching groove 171 and is engaged in the latching groove 171, thereby connecting the mouthpiece 170 to the housing 120. The clamping member 180 has an annular shape. The clamping member 180 is located at the junction between the mouthpiece 170 and the housing 120, and the clamping member 180 is sleeved on an outside of the mouthpiece 170 and the housing 120. Preferably, the latching portion 125 and the latching groove 171 are both annular. Preferably, the inner sidewall of the latching groove 171 is provided with the protruding hook 1711, and the latching portion 125 defines the groove 1251 corresponding to the hook 1711. Preferably, the hook 1711 is adjacent to an end of the mouthpiece 170.

The clamping member 180 can be made of metal, such as brass. Brass is an alloy containing copper and zinc, it has a high strength, large hardness, and improved wear resistance. The brass also has a prominent mechanical property during processing and a low cost. Of course, in alternative embodiments, the mouthpiece 170 can be formed by an end of the housing 120 away from the core body 141, i.e., the housing 120 and the mouthpiece 170 are integrated formed, thus the clamping member 180 can be omitted.

Figure 14:
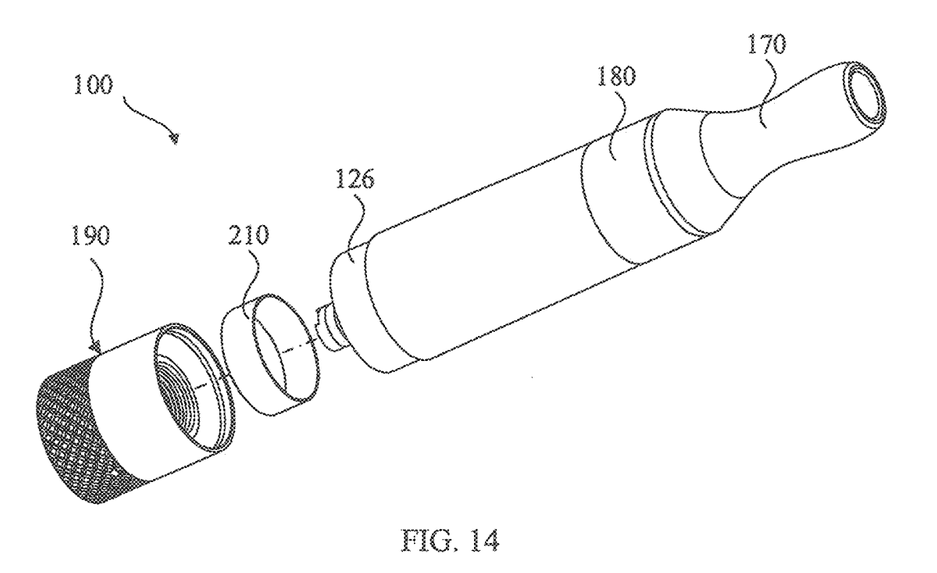
FIG. 14 is another exploded view of the atomizing assembly of the inhaler of FIG. 1.

Referring also to FIG. 3 and FIG. 14, in one embodiment, the atomizing assembly 100 further includes a connecting member 190 and a support member 210. The connecting member 190 is connected to the core body 141 and includes an annular sheath portion 1911, which is tightly sleeved on an outside of the housing 120. The support member 210 has an annular shape and is located in the reservoir 122. The support member 210 abuts an inner sidewall of the first tubular structure 123, and the support member 210 is located corresponding to the sheath portion 1911. In one embodiment, the housing 120 is provided with a stepped portion 126 on an outside thereof. The stepped portion 126 is latched with the sheath portion 1911, therefore on the one hand, it is convenient for the connecting member 190 to be positioned, i.e., it is convenient to determine whether the connecting member 190 is already in a preset position; on the other hand, the outer sidewall of the sheath portion 1911 may be coplanar with the outer sidewall of the housing 120, thus the atomizing element 100 has a overall flat appearance.

The connecting member 190 can be used to connect the atomizing assembly 100 to the other components of the inhaler. The support member 210 can reinforce the connection between the connecting member 190 and the housing 120. The support member 210 is a rigid support element. The first tubular structure 123 of the housing 120 is clamped between the support member 210 and the sheath portion 1911. The sheath portion 1911 is tightly sleeved on the outside of the first tubular structure 123, and the sheath portion 1911 is in close contact with an end of the first tubular structure 123. If the support member 210 is not provided, the end of the first tubular structure 123 is easily deformed by pressing for a long time, such that the connection is easily loosened. In the illustrated embodiment, the support member 210 is received in the interior of the first tubular structure 123, thus the end of the first tubular structure 123 will not be deformed, such that the fixing connection between the connecting member 190 and the housing 120 will become more secured. Even if the inhaler falls to the ground, the connecting member 190 and the housing 120 will not be disengaged.

The hardness of the support member 210 is generally greater than that of the housing 120. The support member 210 is preferably a steal ring formed by stretching a profile, for it has a low price. The steal ring is easy to be processed to be thin, such as having a thickness of 0.2 mm. The steal ring requires occupying space in the reservoir 122, thus the smaller the volume of the steel ring, the smaller the effect to the volume of the reservoir 122. If the inhaler is an electronic cigarette, the liquid in the reservoir 122 is less corrosive to the steel ring, however, if the inhaler is a medical nebulizer, the liquid medicine may corrode the steal ring. The outer circumference of the steel ring may be provided with a spacer or may be coated with an isolation paint to prevent the steel ring from chemically reacting with the liquid in the reservoir 122.

Figure 15:
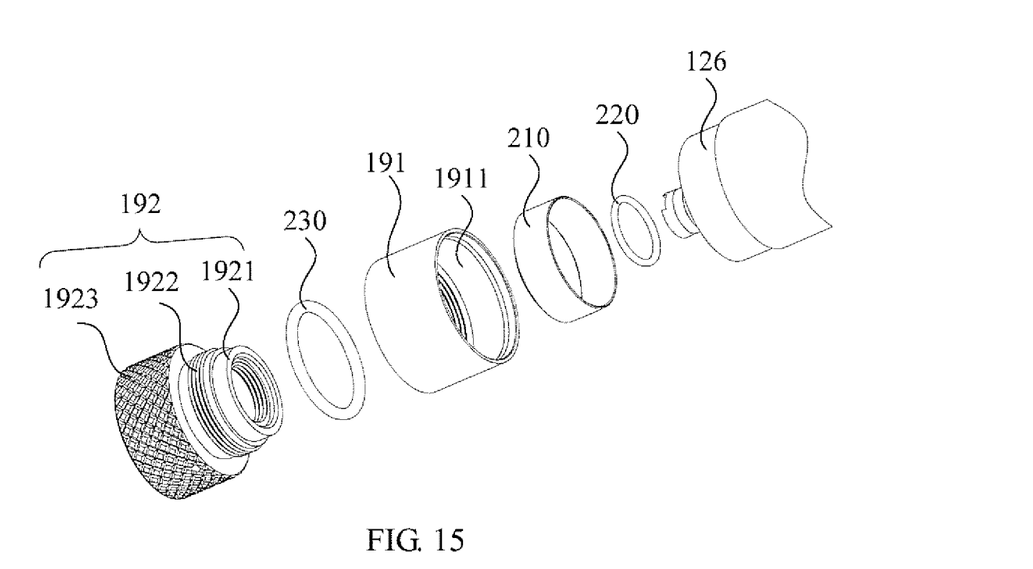
FIG. 15 is an partial exploded view of the atomizing assembly of the inhaler of FIG. 14.
Figure 16:
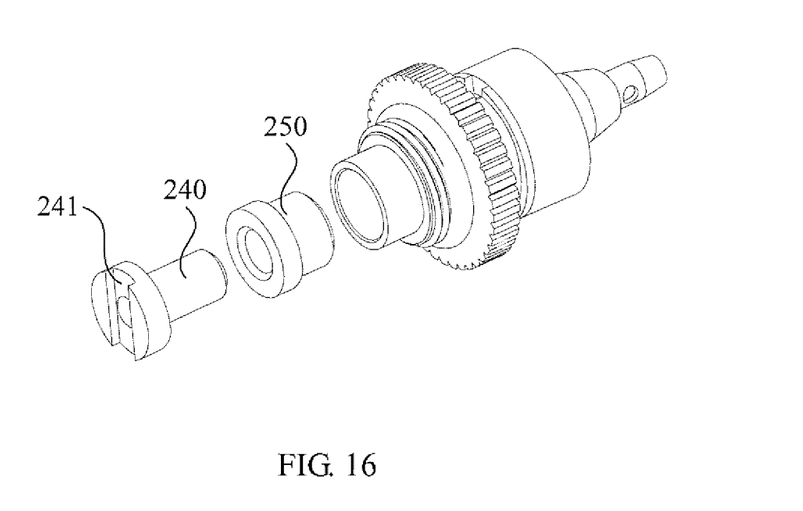
FIG. 16 is another exploded view of the atomizing core of the atomizing assembly of the inhaler of FIG. 1.

Referring also to FIG. 3 and FIG. 15, further in one embodiment, the connecting member 190 can include a first connecting member 191 and a second connecting member 192. The sheath portion 1911 can be located on the first connecting member 191. The first connecting member 191 is provided with an inner screw thread, and the second connecting member 192 is provided with an outer screw thread engaging the inner screw thread of the first connecting member 191. The first connecting member 191 is threadedly connected the second connecting member 192. The second member 192 is also provided with an inner screw thread, the core body 141 is provided with an outer screw thread engaging at least partial inner screw thread of the second connecting member 192. The second connecting member 192 is threadedly connected to the core body 141, thus fixing the core body 141 to the housing 120.

Partial inner screw thread of the second connecting member 192 can be threadedly connected to the power source assembly of the inhaler. In one embodiment, the inner screw thread of the second connecting member 192 includes two segments. One segment of the second connecting member 192 is configured to be threadedly connected to the core body 141, the other segment of the second connecting member 192 is configured to be threadedly connected to the power source assembly. Since the first connecting member 191 and the second connecting member 192, the second connecting member 192 and the core body 141 are threadedly connected, such that the core body 141 can be easily assembled or disassembled, thus facilitating replacing the core body 141 or filling liquid to the reservoir. Therefore the atomization assembly 100 can be reused, thus reducing cost.

In the aforementioned embodiments, the first connecting member 191 is connected to the housing 120 by configuring the sheath portion 1911, besides that, in alternative embodiments, the fixing connection between the first connecting member 191 and the housing 120 can be in other forms. One fixing connection can be a threaded connection, e.g., the housing 120 is provided with an outer screw thread, and the first connecting member 191 is provided with an inner screw thread matching the outer screw thread. Alternatively, the housing 120 is provided with an inner screw thread, and the first connecting member 191 is provided with an outer screw thread matching the inner screw thread, such that the first connecting member 191 is threadedly fixed to the housing 120. Another fixing connection between the first connecting member 191 and the housing 120 can be implemented via a screw, e.g., both of the first connecting member 191 and the housing 120 define screw holes, and the first connecting member 191 and the housing 120 are fixed via the screw extending through the corresponding screw holes. Another fixing connection between the first connecting member 191 and the housing 120 can be implemented via a snap, e.g., the housing 120 is provided with a snapping portion, and the first connecting member 191 defines a snapping groove corresponding to the snapping portion. Alternatively, the first connecting member 191 is provided with a snapping portion, and the housing 120 defines a snapping groove corresponding to the snapping portion. The snapping portion is engaged in the snapping groove, such that the first connecting member 191 is fixed to the housing 120. In an alternative embodiment, the first connecting member 191 and the housing 120 are integrated formed.

Further, Referring to FIG. 3 and FIG. 15, in one embodiment, the second connecting member 192 may include a first portion 1921, a second portion 1922, and a third portion 1923, which are successively connected to each other. The first portion 1921, the second portion 1922, and the third portion 1923 are hollow cylinders. The first portion 1921, the second portion 1922, and the third portion 1923 are coaxially arranged. The first portion 1921 has a diameter less than that of the second portion 1922, and the second portion 1922 has a diameter less than that of the third portion 1923. The first portion 1921 is threadedly connected to the core body 141, and an end of the first portion 1921 abuts an annular flange 144. The second portion 1922 is threadedly connected to the first portion 1921, and an end of the first connecting member 1921 abuts the third portion 1923.

In one embodiment, a sealing ring 220 is provided between the second connecting member 192 and the core body 141, so as to prevent leakage of the liquid from a gap between the second connecting member 192 and the core body 141. Referring also to FIG. 4 to FIG. 6, furthermore, the atomizing core 140 can include an annular flange 144, which is fixed on the core body 141. The annular flange 144 abuts the end of the second connecting member 192. The sealing ring 220 is positioned at a corner between the annular flange 144 and the core body 141 adjacent to the second connecting member 192. The sealing ring 220 abuts the annular flange 144, the core body 141, and the second connecting member 192 at the same time. By configuring the sealing ring 220 at this position, a better sealing effect can be obtained. Meanwhile, since the annular flange 144 abuts the end of the second connecting member 192, when the second connecting member 192 rotates, it can prevent the screw thread from being damaged due to excessive force. In a preferable embodiment, a sealing member 230 is provided between the first connecting member 191 and the second connecting member 192, thus preventing leakage of the liquid from a gap between the first connecting member 191 and the second connecting member 192. The sealing member 230 is positioned at a corner of the second portion 1922 and the third portion 1923, such that the sealing member 230 abuts the second portion 1922, the third portion 1923, and the first connecting member 191 at the same time. By configuring the sealing ring 230 at this position, a better sealing effect can be obtained.

The foregoing sealing ring can fit the atomizing core 140 and the connecting member 190, thus the reservoir 122 is effectively sealed. Even if the atomizing core 140 is assembled or disassembled for a plurality of times, the sealing performance of the atomizing assembly 100 as a whole will not be affected.

The atomizing assembly 100 is normally connected to the power source assembly of the inhaler, the power source assembly is electrically coupled to the atomizing element 143 to provide power for atomization. In one embodiment, the core body 141 and the second connecting member 192 are both conductors, a negative lead of the atomizing element 143 is electrically coupled to the core body 141, the core body 141 is electrically coupled to the second connecting member 192, the second connecting member 192 is electrically coupled to the power source assembly. The voltage required by the atomizing element 143 is generally low and the current is small, the negative electrode of the power source can be in contact with the user.

Further, referring to FIG. 3 to FIG. 6 and FIG. 16, in one embodiment, the atomizing assembly 100 further includes an inlet tube 240 and an insulating sleeve 250. The inlet tube 240 is a conductor, which is located at the inlet 1412 of the core body 141. The inlet tube 240 is configured to be electrically coupled to the power source assembly. Preferably, the inlet tube 240 defines a ventilation slot 241 at an end thereof, such that the problem that air cannot enter the atomizing core when the end of the inlet tube 240 abuts the power source assembly can be solved. The insulating sleeve 250 is located between the inlet tube 240 and the inner sidewall of the core body 141, thus isolating the inlet tube 240 from the core body 141. The insulating sleeve 250 is generally made of silicone material having elasticity, thus it also has a sealing function. The positive lead wire can be located between the inlet tube 240 and the insulating sleeve 250, and the positive lead wire is electrically coupled to the inlet tube 240. The negative lead wire can be located between the insulating sleeve 250 and the inner wall of the core body 141, and the negative lead wire is electrically coupled to the core body 141. The insulating sleeve 250 has elasticity and can press the lead wire, thus ensuring connection reliability.

Figure 17:
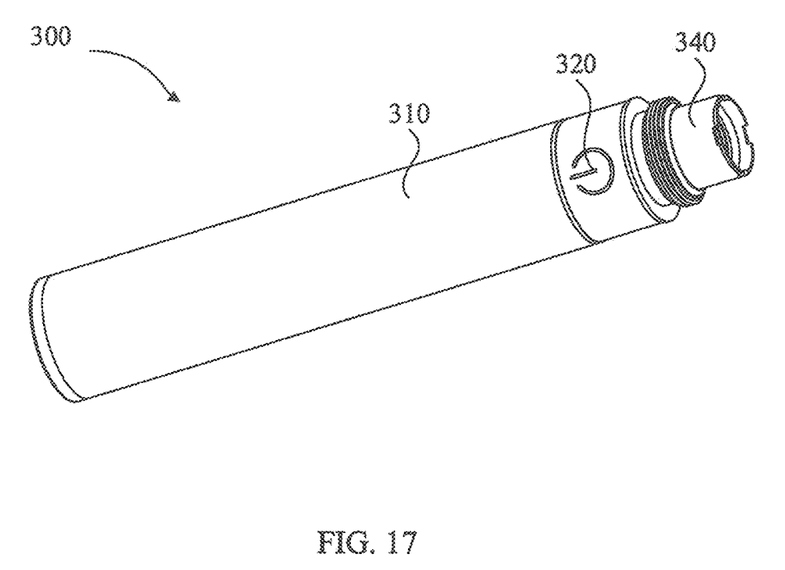
FIG. 17 is a perspective view of a power source of an inhaler according to an embodiment.
Figure 18:
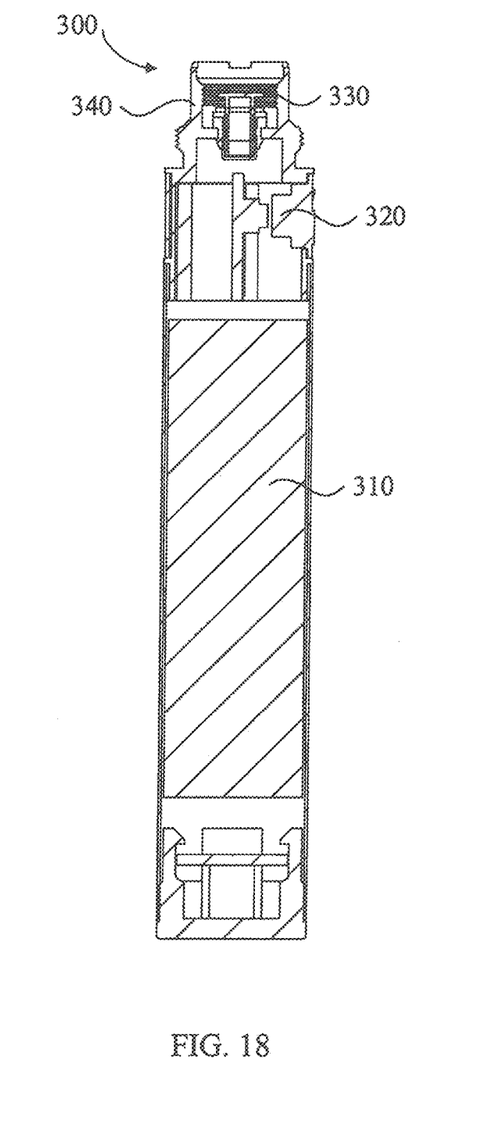
FIG. 18 is a cross-sectional view of the power source of the inhaler of FIG. 17.

In one embodiment, the inhaler includes the power source assembly 300 shown in FIG. 17 and FIG. 18, and the atomizing assembly 100 shown in FIG. 1 to FIG. 16. The power source assembly 300 can be fixed to the atomizing assembly 100, and the power source assembly 300 is electrically coupled to the atomizing assembly 100. The inhaler is used to atomize the liquid, and to deliver the atomized liquid into the human body. The inhaler can be an electronic cigarette, or a medical nebulizer and the like.

The sidewall of the exhaust pipe 142 defines the through hole 1422 in fluid communication with the interior of the exhaust pipe 142 and the airflow channel 121. The through hole 1422 can enable the condensed liquid in the airflow channel 121 to return to the atomizing chamber 1411, thus preventing the liquid from forming a film at an end opening of the exhaust pipe 142 due to the large viscosity and surface tension of the liquid, and the film can block the liquid from flowing back from the end opening of the exhaust pipe 142 to the atomizing chamber 1411. The liquid will not accumulate in the airflow channel 121, such that the problem of making noise and easily drawing fluid into the mouth by the user during use can be solved.

In one embodiment, the power source assembly 300 includes a main body 310, a power switch 320, a positive electrode connecting portion 330, and a negative electrode connecting portion 340. The negative electrode connecting portion 340 is connected to the main body 310, the positive electrode connecting portion 330 is provided with an outer screw thread, which can be adapted to the inner screw thread of the second connecting member 192 of the atomizing assembly 100, such that the negative electrode connecting portion 340 is threadedly connected to the second connecting member 192. The power source assembly 300 and the atomizing assembly 100 can be easily assembled and disassembled. Therefore, when the power source assembly 300 is short of power, the power source assembly 300 can be replaced or charged by disassembly. When the liquid in the atomizing assembly 100 is insufficient, it can be replaced in time.

The positive electrode connecting portion 330 can be located at a middle portion of the negative electrode connecting portion 340. An insulating spacer or an insulating layer is provided between the positive electrode connecting portion 330 and the negative electrode connecting portion 340, alternatively, the positive electrode connecting portion 330 is not in contact with the negative electrode connecting portion 340. After the negative electrode connecting portion 340 is threadedly connected to the the second connecting member 192, the positive electrode connecting portion 330 can abut and be electrically coupled to the inlet tube 240 of the atomizing assembly 100. There is a relatively large contact area between the positive electrode connecting portion 330 and the atomizing assembly 100, thereby improving the reliability of the positive electrode electrical connection. The power switch 320 can be located on the main body 310. The circuit conduction can be controlled through the switch, thus it is convenient to use. The user can turn off the power at any time, thus saving power.

Although the description is illustrated and described herein with reference to certain embodiments, the description is not intended to be limited to the details shown. Modifications may be made in the details within the scope and range equivalents of the claims.

What is claimed is:

1. An atomizing assembly for an inhaler, comprising:
a housing defining an airflow channel therein and comprising a reservoir surrounding the airflow channel for storing liquid; and
an atomizing core coupled to the housing and comprising a core body, an exhaust pipe, and an atomizing element, the core body defining an atomizing chamber therein, the core body further defining an inlet and an outlet thereon in fluid communication with the atomizing chamber, the exhaust pipe being located at the outlet, the atomizing element being received in the atomizing chamber and being configured to atomize the liquid;

wherein the core body further defines a liquid absorbing hole in fluid communication with the atomizing chamber and the reservoir, the atomizing element is in contact with the liquid in the reservoir via the liquid absorbing hole, the exhaust pipe extends at least partially into the airflow channel, the exhaust pipe defines a through hole or notch on a sidewall thereof which is in fluid communication with an interior of the exhaust pipe and the airflow channel;

wherein the housing comprises a first tubular structure and a second tubular structure, the first tubular structure has a greater diameter than a diameter of the second tubular structure, the second tubular structure is located inside the first tubular structure, the airflow channel is formed by an interior of the second tubular structure, the reservoir is formed between the second tubular structure and the first tubular structure;

wherein the atomizing core further comprises a sealing member sleeved on the exhaust pipe; the sealing member is located between the exhaust pipe and the second tubular structure and abuts an inner sidewall of the second tubular structure; a portion of the exhaust pipe extends out of the sealing member; the through hole is located at a portion of the exhaust pipe extending out of the sealing member and is adjacent to the sealing member.

2. The atomizing assembly for the inhaler according to claim 1, further comprising:
a connecting member connected to the core body, wherein the connecting member comprises an annular sheath portion tightly sleeved to an outside of the housing; and
a support member having an annular shape and located in the reservoir, wherein the support member abuts an inner sidewall of the first tubular structure and the support member is located corresponding to the sheath portion.

3. The atomizing assembly for the inhaler according to claim 2, wherein the housing is provided with a stepped portion on an outside thereof; the stepped portion is latched with the sheath portion.

4. The atomizing assembly for the inhaler according to claim 2, wherein the connecting member comprises a first connecting member and a second connecting member, the sheath portion is located on the first connecting member, the first connecting member is provided with an inner screw thread, and the second connecting member is provided with an outer screw thread engaging the inner screw thread of the first connecting member, the first connecting member is threadedly connected the second connecting member, the second member is provided with an inner screw thread, the core body is provided with an outer screw thread engaging at least partial inner screw thread of the second connecting member, the second connecting member is threadedly connected to the core body.

5. The atomizing assembly for the inhaler according to claim 4, wherein the first connecting member and the second connecting member are provided with a sealing ring therebetween;

and/or the second connecting member and the core body are provided with a sealing ring therebetween.

6. The atomizing assembly for the inhaler according to claim 4, wherein the second connecting member comprises a first portion, a second portion, and a third portion, wherein the first portion, the second portion and the third portion are successively connected such that the second section is connected to the first section and the third section is coupled to the second section; the first portion, the second portion, and the third portion are hollow cylinders and are coaxially arranged, the first portion has a less diameter than a diameter of the second portion, the second portion has a less diameter than a diameter of the third portion, the first portion is threadedly connected to the core body, the second portion is threadedly connected to the first portion, and an end of the first connecting member abuts the third portion.

7. The atomizing assembly for the inhaler according to claim 4, wherein the atomizing core further comprises an annular flange fixed on the core body, and the annular flange abuts an end of the second connecting member.

8. The atomizing assembly for the inhaler according to claim 1, wherein the notch is defined at an edge of the exhaust pipe, the notch is part of a plurality of notches, wherein the plurality of notches are serratedly arranged on the edge of the exhaust pipe.

9. The atomizing assembly for the inhaler according to claim 1, wherein the housing forms a mouthpiece at an end thereof away from the core body; or the atomizing assembly further comprises a mouthpiece located at an end of the housing away from the core body.

10. The atomizing assembly for the inhaler according to claim 1, further comprising:
a mouthpiece located at an end of the housing away from the core body, wherein the mouthpiece defines an annular depressed latching groove at an end thereof the housing is provided with an annular protruded latching portion at an end thereof away from the core body, the annular protruded latching portion matches the annular depressed latching groove and is engaged in the latching groove, thereby connecting the mouthpiece to the housing;
a clamping member that is annular, wherein the clamping member is located between the mouthpiece and the housing, and the clamping member is sleeved on an outside of the mouthpiece and the housing.

11. The atomizing assembly for the inhaler according to claim 10, wherein an inner sidewall of the latching groove is provided with a protruding hook, and the latching portion defines a groove corresponding the hook.

12. The atomizing assembly for the inhaler according to claim 11, wherein the hook is positioned adjacent to the end of the mouthpiece.

13. An inhaler, comprising a power source assembly and an atomizing assembly for an inhaler according to claim 1; wherein the power source assembly is fixed to the atomizing assembly, and the power source assembly is electrically coupled to the atomizing element.

* * * * *